United States Patent
Khalili et al.

(10) Patent No.: US 10,690,668 B2
(45) Date of Patent: Jun. 23, 2020

(54) METHOD FOR DETECTING POLYOMAVIRUS REACTIVATION

(71) Applicant: TEMPLE UNIVERSITY—OF THE COMMONWEALTH SYSTEM OF HIGHER EDUCATION, Philadelphia, PA (US)

(72) Inventors: Kamel Khalili, Bala Cynwyd, PA (US); Ilker K. Sariyer, Upper Darby, PA (US)

(73) Assignee: Temple University—Of The Commonwealth System Of Higher Education, Philadelphia, PA (US)

( * ) Notice: Subject to any disclaimer, the term of this patent is extended or adjusted under 35 U.S.C. 154(b) by 0 days.

(21) Appl. No.: 14/375,263

(22) PCT Filed: Jan. 29, 2013

(86) PCT No.: PCT/US2013/023618
§ 371 (c)(1),
(2) Date: Jul. 29, 2014

(87) PCT Pub. No.: WO2013/116210
PCT Pub. Date: Aug. 8, 2013

(65) Prior Publication Data
US 2015/0010901 A1    Jan. 8, 2015

Related U.S. Application Data (60) Provisional application No. 61/592,402, filed on Jan. 30, 2012.

(51) Int. Cl.
*G01N 33/53* (2006.01)
*G01N 33/569* (2006.01)

(52) U.S. Cl.
CPC . *G01N 33/56983* (2013.01); *G01N 2333/025* (2013.01); *G01N 2469/10* (2013.01);
(Continued)

(58) Field of Classification Search
None
See application file for complete search history.

(56) References Cited

U.S. PATENT DOCUMENTS

| | | |
|---|---|---|
| 7,612,039 B2 | 11/2009 | Khalili |
| 2004/0259767 A1 | 12/2004 | Nagashima et al. |
| 2009/0099335 A1 | 4/2009 | Lacey |

FOREIGN PATENT DOCUMENTS

| | | |
|---|---|---|
| JP | 2005-341864 A | 12/2005 |
| WO | 92/19774 A1 | 11/1992 |

OTHER PUBLICATIONS

Myhre et al., "Clinical polyomavirus BK variants with agnogene deletion are non-functional but rescued by trans-complementation," Virology 398: 12-20 (2010)).*

(Continued)

*Primary Examiner* — Janet L Andres
*Assistant Examiner* — Stuart W Snyder
(74) *Attorney, Agent, or Firm* — Faegre Drinker Biddle & Reath LLP (57) ABSTRACT

The invention provides methods of detection and monitoring of polyomavirus reactivation and active polyomavirus infections using a biological fluid sample. Also provided are methods of risk assessment and risk monitoring of developing a polyomavirus-associated disease.

9 Claims, 6 Drawing Sheets

(52) U.S. Cl.
CPC ..... *G01N 2469/20* (2013.01); *G01N 2800/50* (2013.01); *G01N 2800/56* (2013.01)

(56) References Cited

OTHER PUBLICATIONS

Del Valle et al., "Detection of Human Polyomavirus Proteins, T-Antigen and Agnoprotein, in Human Tumor Tissue Arrays," Journal of Medical Virology 82: 806-811 (2010).*
Delbue et al., "A Case of progressive multifocal leukoencephalopathy patient with four different JC virus transcriptional control region rearrangements in cerebrospinal fluid, blood, serum, and urine," Journal of Neurovirology 11: 51-57 (2005).*
Egli et al., "Prevalence of Polyomavirus BK and JC Infection and Replication in 400 Healthy Blood Donors," The Journal of Infectious Diseases 199: 837-46 (2009).*
Slavov et al., "Molecular Virology and Clinical Aspects of the Human Polyomavirus BK Infection," Biotechnology & Biotechnological Equipment, 20:2:9-16 (2006).*
Cold Spring Harbor Monograph Archive, "5 The Lytic Cycle of Polyoma Virus and SV40," The Molecular Biology of Tumour Viruses, vol. 03 (1973).*
Chen et al., "Kinetic Analysis of the Steps of the Polyomavirus Lytic Cycle," Journal of Virology,8368-8379 (2001).*
Rinaldo et al., "The Agnogene of the Human Polyomavirus BK Is Expressed," Journal of Virology, vol. 72, No. 7: 6233-6236 (1998).*
Berg et al., "Section 4.3, Immunology Provides Important Techniques with Which to Investigate Proteins," Biochemistry, 5th Edition, New York W H Freeman, Available from: https://www.ncbi.nlm.nih.gov/books/NBK22420/ (2002).*
Otlu et al. The agnoprotein of Polyomavirus JC is Released by Infected Cells: Evidence for Its Cellular Uptake by Uninfected Neighboring Cells. Virology. Nov. 2014; 88-95.*
Del Valle and Khalili, Detection of Human Polyomavirus Proteins, T-Antigen and Agnoprotein, in Human Tumor Tissue Arrays. J. Med. Virol. 2010; 82:806-811.*
Delbue et al., A case of a progressive multifocal leukoencephalopathy patient with four different JC virus transcriptional control region rearrangements in cerebrospinal fluid, blood, serum, and urine. J. NeuroVirol. 2005; 11: 51-57.*
Merabova et al., JC Virus Agnoprotein Inhibits In Vitro Differentiation of Oligodendrocytes and Promotes Apoptosis, J. Virol. 2008; vol. 82(3):1558-1569.*
Del Valle et al. "Detection of JC Virus DNA Sequences and Expression of Viral T Antigen and Agnoprotein in Esophageal Carcinoma" Cancer, 103(3):516-527 (2005).
Egli et al. "Polyomavirus BK after Kidney Transplantation—Role of Molecular and Immunologic Markers" Trends in Transplant, 3:85-102 (2009).
Gerits et al. "Agnoprotein of mammalian polyomaviruses" Virology, 432:316-326 (ePub Jun. 21, 2012).
Guillaume et al. "Progressive multifocal leukoencephalopathy: simultaneous detection of JCV DNA and anti-JCV antibodies in the cerebrospinal fluid" European Journal of Neurology, 7:101-106 (2000).

Leuenberger et al. "Human Polyomavirus Type 1 (BK Virus) Agnoprotein Is Abundantly Expressed but Immunologically Ignored" Clinical and Vaccine Immunology, 14(8):959-968 (Aug. 2007).
Okada et al. "Expression of JC virus agnoprotein in progressive multifocal leukoencephalopathy brain" Acta Neuropathol, 104:130-136 (2002).
Tavazzi et al. "Progressive multifocal leukoencephalopathy: an unexpected complication of modern therapeutic monoclonal antibody therapies" Clinical Microbiology and Infection, 17(12):1776-1780 (ePub Nov. 2011).
Weber et al. "Analysis of the Systemic and Intrathecal Humoral Immune Response in Progressive Multifocal Leukoencephalopathy" Journal of Infectious Diseases, 176:250-254 (1997).
White et al. "Pathogenesis of Progressive Multifocal Leukoencephalopathy—Revisited" Journal of Infectious Diseases, 203:578-586 (2011).
Bialasiewicz, S., et al., 2009, "Detection of BK, JC, WU, or KI polyomaviruses in faecal, urine, blood, cerebrospinal fluid and respiratory samples", J Clin Virol., 45(3) :249-54.
Cinque, P., et al., 2009, "Progressive Multifocal Leukoencephalopathy Complicating HIV-1 Infection", Lancet Infect Dis., 9(10): 625-636.
Coelho, T., et al., 2010, "JC virus in the pathogenesis of colorectal cancer, an etiological agent or another component in a multistep process"?, Virol J., 7: 42, Epub Feb. 18, 2010; doi:10.1186/1743-422x-7-42.
Del Valle, L., et al., 2002, "Expression of Human Neurotropic Polyomavirus JCV Late Gene Product Agnoprotein in Human Medulloblastoma", Journal of the National Cancer Institute, vol. 94, No. 4.
Khalili, K., et al., 2005, "The Agnoprotein of Polyomaviruses: A Multifunctional Auxiliary Protein", Journal of Cellular Physiology, 204: 1-7.
Moens, U., et al., "Human Polyomaviruses in Skin Diseases", Pathology Research International, vol. 2011, Article ID 123491, 12 pages; doi:10.4061/2011/123491.
Okada Y., et al., 2001, "Distribution and function of JCV agnoprotein", J Neurovirol, 7(4) :302-306.
Okada, Y., et al., 2002, "Expression of JC virus agnoprotein in progressive multifocal leukoencephalopathy brain", Acta Neuropathol, 104: 130-136.
Okada, Y., et al., 2005, "Dissociation of heterochromatin protein 1 from lamin B receptor induced by human polyomavirus agnoprotein: role in nuclear egress of viral particles", EMBO reports, vol. 6, No. 5, 452-457.
Safak, M., et al., 2002, "Functional Interaction between JC Virus Late Regulatory Agnoprotein and Cellular Y-Box Binding Transcription Factor, YB-1", J Virol, v.76(8): 3828-3838.
Seth, P., et al., 2003, "Advances in the biology of JC virus and induction of progressive multifocal leukoencephalopathy", Journal of NeuroVirology, 9: 236-246.
Suzuki, T., et al., 2005, "Identification of FEZ1 as a Protein That Interacts with JC Virus Agnoprotein and Microtubules", The Journal of Biological Chemistry, vol. 280, No. 26, pp. 24948-24956.
Suzuki, T., et al., 2010, "The Human Polyoma JC Virus Agnoprotein Acts as a Viroporin", PLoS Pathogens, vol. 6, Issue 3.
Bialasiewicz et al, "Detection of BK, JC, WU, or KI polyomaviruses in faecal, urine, blood, cerebrospinal fluid and respiratory samples," 45(3): 249-254 (2009).

* cited by examiner

METHOD FOR DETECTING POLYOMAVIRUS REACTIVATION

CROSS-REFERENCE TO RELATED APPLICATIONS

The benefit of the filing date of U.S. Provisional Patent Application No. 61/592,402, filed Jan. 30, 2012, is hereby claimed. The entire disclosures of the aforesaid application is incorporated herein by reference.

FIELD OF THE INVENTION

This invention relates to detection of polyomavirus reactivation and assessment of risk for developing polyomavirus-induced diseases.

BACKGROUND OF THE INVENTION

Polyomavirus is the genus of the viruses within the family Polyomaviridae. Nine polyomaviruses have been discovered in humans; JCV, BKV, KI virus and WU virus, Merkel cell polyomavirus (MCV), Trichodysplasia sinulosa-associated polyomavirus (TSV), HPyV6, HPyV7, and HPyV9. Among these human polyomaviruses, JCV, BKV, and MCV cause serious complications and diseases. MCV is shown to cause a rare but serious form of skin cancer, merkel cell carcinoma. BKV produces a serious infection of the kidneys of immunosuppressed transplant patients which is a significant basis of graft loss. BKV has a high prevalence in the human population and establishes persistent life long latent infection, typically without clinical symptoms.

Among the human polyomaviruses, JCV is the most abundant polyomavirus which infects more than 80% of the human population during childhood (also typically without clinical symptoms), and establishes a persistent life long latent infection. Reactivation of JCV, which replicates in glial cells in the brain, can cause the fatal demyelinating disease, progressive multifocal leukoencephalopathy (PML), which is usually seen in patients with underlying immunocompromised conditions, notably among AIDS patients and those on chronic immunosuppressive regimens.

Little is known about the progression of PML since there is no biomarker for the detection of JCV reactivation and infection in affected individuals. Most PML cases are diagnosed in patients at a late stage of the disease after the onset of the neurological complications. There are no established diagnostic markers applicable to the clinic to predict which patients will develop the disease.

Polyomaviruses such as JCV are non-enveloped, double-stranded DNA viruses. The DNA comprises an early coding region and a late coding region. The early region encodes two oncoproteins called large T antigen (T-Ag) and small t antigen (t-Ag). The late region encodes three capsid proteins, VP1, VP2, and VP3. The detection of polyomavirus DNA and/or anti-polyomavirus antibodies in bodily fluids have been explored as possible methods of diagnosis of polyomavirus reactivation. However, due to the persistent life long infection, such methods have proven somewhat unreliable.

In a subset of polyomaviruses, the late region also encodes a small regulatory protein called agnoprotein. Agnoprotein plays a role in regulation of viral gene expression and replication, and in the modulation of some host cell functions (see, e.g., Khalili et al., *J Cell Physiol.* 204:1-7, 2005). Agnoprotein is a small, integral membrane protein and is produced late in the infectious cycle (see, e.g, Suzuki et al., *PLoS Pathog* 6(3):e1000801 doi:10.1371/kpirma; .ppat.100801, 2010). In brain tissue samples from patients with PML, agnoprotein is detected in the perinuclear area and cytoplasmic region of cells in demyelinated lesions, but was not detected in normal areas of the PML brain tissues or in normal brains (Okada et al., *Acta Neuropathol* 104:130-136, 2002). These data led to the suggestion that such detection of agnoprotein may be useful for diagnosis of PML (Okada et al, 2002, supra). A tissue biopsy, is an invasive technique and is associated with pain as well as risk of infection, hemorrhage, damage to healthy tissue, and related complications.

What is needed is a simple and easy method for detection of polyomavirus reactivation and active infection in patients at risk, for instance, of developing polyomavirus-induced diseases, including but not limited to, PML.

SUMMARY OF THE INVENTION

The invention is based on the discovery that polyomavirus agnoprotein is secreted from cells having an active polyomavirus infection and can be detected in body fluids, such as blood, urine, and cerebrospinal fluid.

In one embodiment, the invention provides a method for detection of polyomavirus reactivation in a patient having or suspected of having a latent polyomavirus infection. The method comprises determining the presence or absence of a polyomavirus agnoprotein and/or the presence or absence of agnoprotein antibodies in the biological sample. The presence of the polyomavirus agnoprotein or agnoprotein antibodies is indicative of reactivation of the polyomavirus in the patient.

In one aspect, the method for detection of polyomavirus reactivation in a patient further comprises measuring the level of the polyomavirus agnoprotein or agnoprotein antibodies in the biological sample, and comparing the level of the polyomavirus agnoprotein or agnoprotein antibodies in the biological sample to the level of polyomavirus agnoprotein or agnoprotein antibodies in a control sample. An elevated level of the polyomavirus agnoprotein or agnoprotein antibodies in the biological sample relative to the level of polyomavirus agnoprotein or agnoprotein antibodies in the control sample is indicative of reactivation of the polyomavirus in the patient.

In another aspect, the method for detection of polyomavirus reactivation in a patient further comprises measuring the level of the polyomavirus agnoprotein or agnoprotein antibodies in the biological sample, and comparing the level of the polyomavirus agnoprotein or agnoprotein antibodies in the biological sample to the level of polyomavirus agnoprotein or agnoprotein antibodies in a positive control sample. A level of the polyomavirus agnoprotein or agnoprotein antibodies in the biological sample that is comparable to the level of polyomavirus agnoprotein or agnoprotein antibodies in the positive control sample is indicative of reactivation of the polyomavirus in the patient.

In another embodiment, the invention provides a method for detecting an active polyomavirus infection in a patient. The method comprises determining the presence or absence of a polyomavirus agnoprotein and/or the presence or absence of agnoprotein antibodies in a biological sample from the patient. The presence of the polyomavirus agnoprotein or agnoprotein antibodies in the biological sample is indicative of an active polyomavirus infection in the patient.

In one aspect, the method for detecting an active polyomavirus infection further comprises measuring the level of the polyomavirus agnoprotein or agnoprotein antibodies in the biological sample, and comparing the level of the polyomavirus agnoprotein or agnoprotein antibodies in the biological sample to the level of polyomavirus agnoprotein or agnoprotein antibodies in a control sample. An elevated level of the polyomavirus agnoprotein or agnoprotein antibodies in the biological sample relative to the level of polyomavirus agnoprotein or agnoprotein antibodies in the control sample is indicative of an active polyomavirus infection in the patient.

In another aspect, the method for detecting an active polyomavirus infection further comprises measuring the level of the polyomavirus agnoprotein and/or agnoprotein antibodies in the biological sample, and comparing the level of the polyomavirus agnoprotein or agnoprotein antibodies in the biological sample to the level of polyomavirus agnoprotein or agnoprotein antibodies in a positive control sample. A level of the polyomavirus agnoprotein or agnoprotein antibodies in the biological sample that is comparable to the level of polyomavirus agnoprotein or agnoprotein antibodies in the positive control sample is indicative of an active polyomavirus infection in the patient.

In another embodiment, the invention provides a method of monitoring a polyomavirus infection in a patient diagnosed with an active polyomavirus infection. The method comprises the step of assessing the level of a polyomavirus agnoprotein and/or agnoprotein antibodies in a first biological sample from the patient to obtain a baseline level. The method further comprises the step of assessing the level of polyomavirus agnoprotein and/or agnoprotein antibodies in a second biological sample from the patient to obtain a second level, wherein the second biological sample is obtained from the patient at a second time. If the second level is greater than the baseline level, the polyomavirus infection in the patient has progressed.

In yet another embodiment, the invention provides a method for assessing risk of developing a disease associated with a polyomavirus in a patient at risk of developing said disease. The method comprises determining the presence or absence of a polyomavirus agnoprotein and/or the presence or absence of agnoprotein antibodies in a biological sample from the patient. The presence of the polyomavirus agnoprotein and/or agnoprotein antibodies is indicative of increased risk of developing a disease associated with the polyomavirus. The at-risk patient can be selected from an AIDS patient, a patient undergoing immunosuppression therapy, an immunocompromised patient, and a renal transplant patient.

In one embodiment of the method for assessing risk, the polyomavirus is JC virus and the polyomavirus-associated disease is one or more of progressive multifocal leukoencephalopathy (PML), medulloblastoma, oligodendroglioma, astroglioma, glioblastoma, and colon cancer. In another embodiment, the polyomavirus is BK virus and the polyomavirus-associated disease is one or more of nephritis, nephropathy and prostate cancer.

In yet another embodiment, the invention provides a method for monitoring risk of developing a disease associated with a polyomavirus in a patient at risk of developing the disease. The method comprises the step of assessing the level of a polyomavirus agnoprotein and/or agnoprotein antibodies in a first biological sample from the patient to obtain a baseline level. The method further comprises the step of assessing the level of polyomavirus agnoprotein and/or agnoprotein antibodies in a second biological sample from the patient to obtain a second level, wherein the second biological sample is obtained from the patient at a second time. If the second level is greater than the baseline level, the patient has an increased risk of developing a disease associated with the polyomavirus. The at-risk patient can be selected from an AIDS patient, a patient undergoing immunosuppression therapy, an immunocompromised patient, a renal transplant patient.

In one embodiment of the method for monitoring risk, the polyomavirus is JC virus and the polyomavirus-associated disease is one or more of progressive multifocal leukoencephalopathy (PML), medulloblastoma, oligodendroglioma, astroglioma, glioblastoma, and colon cancer. In another embodiment, the polyomavirus is BK virus and the polyomavirus-associated disease is one or more of nephritis, nephropathy and prostate cancer.

The invention further provides a kit for detecting a polyomavirus agnoprotein in a biological sample. The kit comprises (a) a set of reagents that specifically detects for detection of a polyomavirus agnoprotein; and (b) instructions for using the kit to detect polyomavirus agnoprotein and/or agnoprotein antibodies in a body fluid selected from the group consisting of blood, blood serum, blood plasma, and urine. The kit is useful for detection of polyomavirus reactivation, detecting or monitoring an active polyomavirus infection, or assessing or monitoring risk of developing a disease associated with a polyomavirus in a biological sample, wherein the biological sample is a body fluid.

In the various embodiments of the invention, the biological sample is a body fluid. Exemplary biological samples are body fluids selected from the group consisting of blood, blood serum, blood plasma, urine, and cerebrospinal fluid. The polyomavirus can be selected from a from a mammalian polyomavirus, a primate polyomavirus or a human polyomavirus. In preferred embodiments, the polyomavirus is a human polyomavirus such as JC virus or BK virus. The preferred patient is a human patient. In some embodiments of the invention, detecting a polyomavirus agnoprotein comprises an antibody-based assay, an aptamer-based assay, a receptor and ligand assay, an enzyme activity assay, and/or an allosteric regulator binding assay.

BRIEF DESCRIPTION OF THE FIGURES

FIG. 4A shows the results of an agnoprotein enzyme-linked immunosorbent assay of human samples. Agnoprotein was detected in the cerebrospinal fluid of a PML case developed in an HIV-AIDS patient (HIV/PML-CSF). Serum samples of MS patients were also positive for agnoprotein at different draw times representing different stages of disease (7A-D, and 11A-D). Recombinant agnoprotein at 10, 1 and 0.1 picogram concentrations was used as positive control (SS=10 pg agno; SS=1 pg agno; SS=0.10 pg agno). Serum sample from an healthy individual (SS) and PBS (Neg-PBS× 2) were used as negative controls of the experiment.

DEFINITIONS

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent depending on the context in which it is used. As used herein, "about" is meant to encompass variations of ±20% or ±10%, more preferably ±5%, even more preferably ±1%, and still more preferably ±0.1%.

Unless otherwise specified herein, the terms "antibody" and "antibodies" broadly encompass naturally-occurring forms of antibodies (e.g., IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

As used herein, an "instructional material" includes a publication, a recording, a diagram, or any other medium of expression, which can be used to communicate the usefulness of the invention in the kit for determining the progression of a disease. The instructional material of the kit of the invention may, for example, be affixed to a container, which contains a reagent of the invention or be shipped together with a container, which contains a reagent. Alternatively, the instructional material may be shipped separately from the container with the intention that the instructional material and the reagent be used cooperatively by the recipient.

"Measuring" or "measurement," or alternatively "detecting" or "detection," or alternatively "determine" or "determining" means assessing the presence, absence, quantity or amount of either (?) a given substance within a clinical or subject-derived sample, including the derivation of qualitative or quantitative concentration levels of such substances.

"Sample" or "biological sample" as used herein means a biological material isolated from an individual. The biological sample may contain any biological material suitable for detecting the desired biomarker.

"Specifically binds" as used herein in the contexts of an antibody refers to antibody binding to a predetermined antigen with a preference that enables the antibody to be used to distinguish the antigen from others to an extent that permits the assays described herein.

As used herein, the term "subject" or "patient" refers to any animal (e.g., a mammal), including, but not limited to humans, non-human primates, rodents, and the like. Typically, the terms "subject" and "patient" are used interchangeably herein in reference to a human subject.

As used herein, a "normal subject" or "control subject" refers, depending on the context, to a subject not suffering from polyomavirus-induced disease or to a subject not suffering from an active polyomavirus infection.

As used herein, a "control sample" refers to a sample from a control subject or a sample representative of a population of control subjects.

As used herein, a "positive control subject" refers, depending on the context, to a subject that is suffering from polyomavirus-induced disease or to a subject that is suffering from an active polyomavirus infection.

As used herein, a "positive control sample" refers to a sample from a positive control subject or a sample representative of a population of positive control subjects.

"Increased risk of developing polyomavirus-associated disease" is used herein to refer to an increase in the likelihood or possibility of developing a disease associated with a polyomavirus. Exemplary polyomavirus-associated diseases include, but are not limited to, progressive multifocal leukoencephalopathy (PML), tumors such as medulloblastoma, colon cancer, nephritis, nephropathy, and prostate cancer. This risk can be assessed relative to a patient's own risk, or with respect to a reference population that does not have clinical evidence of the disease or to a reference population that does have clinical evidence of the disease. The reference population may be representative of the patient with regard to approximate age, age group, medical conditions, and/or gender.

As used herein, an "active polyomavirus infection" refers to replication of a polyomavirus in a cell. "Polyomavirus replication" refers to any one or more of transcription of the late coding region of the polyomavirus genome, translation of the late coding region RNAs, virion production and virion release. "Reactivation of a polyomavirus" refers to the development of an active polyomavirus infection in a subject having a latent polyomavirus infection.

As used herein, a "latent polyomavirus infection" refers to polyomavirus infection that is not active. A subject having or suspected of having a latent polyomavirus infection includes a subject who has been exposed to a polyomavirus, and/or in whom the presence of polyomavirus DNA and/or anti-polyomavirus antibodies has been clinically detected.

As used herein, "agnoprotein" and "polyomavirus agnoprotein" refer to a small protein encoded in the late coding region of some polyomaviruses, such as JC virus, BK virus and SV40. Agnoprotein is not present in the virion particle. Numerous agnoprotein sequences are known in the art and exemplary sequences are mentioned elsewhere herein by accession number. Polyomavirus agnoprotein are discussed generally, for instance, in Khalili et al., *J Cellular Physiol* 204:1-7, 2005.

As envisioned in the present invention with respect to the disclosed compositions of matter and methods, in one aspect the embodiments of the invention comprise the components and/or steps disclosed herein. In another aspect, the embodiments of the invention consist essentially of the components and/or steps disclosed herein. In yet another aspect, the embodiments of the invention consist of the components and/or steps disclosed herein.

DETAILED DESCRIPTION OF THE INVENTION

Agnoprotein is a small viral regulatory protein expressed by the late coding region of certain polyomaviruses such as the JC virus. Agnoprotein is not incorporated into virions (virus particles). Therefore, agnoprotein can only be detected in cells which actively replicate the virus. Agnoprotein is an integral membrane protein and is localized intracellularly in the perinuclear region and the cytoplasm in cells replicating the virus. Detection of agnoprotein has required tissue samples, such as tissue biopsy samples or related components such cell lysates or subcellular fractions. Unexpectedly, we have found that agnoprotein is secreted from polyomavirus-infected cells undergoing active infection, and may thus serve as a marker for detection of polyomavirus reactivation and replication in patients, for instance in patients at risk of developing polyomavirus-infected diseases, particularly PML. The not heretofore recognized secretion of agnoprotein from cells actively infected with polyomavirus has led to the further discovery that agnoprotein can be detected in body fluids of patients. For instance, we have found that agnoprotein is released from cells infected with polyomavirus, particularly JCV, in that agnoprotein can be detected in biological samples, e.g., serum and urine. This discovery advantageously permits the use of biological body fluid samples, rather than tissue biopsy samples or other tissue extracts, in assays detecting agnoprotein for the detection of polyomavirus reactivation and replication. Assays using a body fluid sample compared to a tissue biopsy are not as invasive, and therefore minimizing possible adverse side effects. Other benefits include reduced cost and possibly more rapid results, and less patient trauma. As such, assays using body fluid samples can be readily employed as routine screening methods for patients at risk, for instance, of developing a polyomavirus-associated disease. Thus the invention also provides assays to assess the risk of developing a polyomavirus-associated disease, such as PML, as well as for monitoring patient status over time, for instance, during an immunosuppressive therapeutic treatment regimen. Thus, the methods of the invention are useful for assessing risk of developing PML.

The assays of the invention can involve the detection of agnoprotein in a biological sample. Moreover, although agnoprotein is not part of polyomavirus virions, secretion of agnoprotein into body fluids during active polyomavirus infection is expected to result in the development of antibodies against agnoprotein in a patient having an active polyomavirus infection. Thus, the assays can also involve the detection of antibodies to agnoprotein in a biological sample.

Biological samples useful in the practicing the methods of the invention are samples of body fluids. Exemplary body fluid samples include blood such as peripheral blood; a blood component such as blood serum ("serum") or blood plasma ("plasma"); urine; spinal fluid such as cerebro-spinal fluid ("CSF"); semen; and lymph. As used herein, "body fluid" excludes tissue biopsy samples such as fixed tissue samples, and fluid samples obtained from tissue such as cell lysates and lysates of subcellular fractions. In preferred embodiments, the biological fluid is one of plasma, serum, urine and CSF. In an embodiment, the biological sample is one of plasma, serum and urine. In an embodiment, the biological sample is one of plasma and serum. The biological fluid is obtained from the subject using conventional methods known in the art. For instance, one skilled in the art knows how to draw blood and how to process it in order to obtain serum and/or plasma for use in the method. In some embodiments, the method of obtaining the biological fluid preferably maintains the integrity of the sample proteins such that agnoprotein, if present, can be accurately quantified in the biological fluid.

In any embodiment of the methods of the invention, the biological sample is selected from the group consisting of blood such as peripheral blood; a blood component such as blood serum ("serum") or blood plasma ("plasma"); urine; spinal fluid such as cerebro-spinal fluid ("CSF"); semen; and lymph. In any embodiment of the methods of the invention, the biological sample is preferably selected from the group consisting of blood, blood serum, blood plasma, urine, and cerebrospinal fluid.

The methods of the invention may be carried out with any subject. The subject is preferably a mammal, more preferably a primate and more preferably still, a human. In some embodiments, the subject has or is suspected of having a latent polyomavirus infection. In one embodiment, the method is employed to determine if the latent infection has progressed to become an active infection. In some embodiments, the patient has been diagnosed with an active polyomavirus infection by other means, and the method of the invention is used to confirm a diagnosis of active polyomavirus infection.

In other embodiments, the methods are carried out with a subject at risk of developing a disease associated with a polyomavirus. Patients at risk of developing a polyomavirus-associated disease include individuals diagnosed with an active polyomavirus infection, individuals diagnosed with an active polyomavirus infection and are immunocompromised, and individuals that are immunocompromised and have or are suspected of having a latent polyomavirus infection. Immunocompromised individuals include: AIDS patients; patients on chronic immunosuppressive treatment regimens, such as organ transplant patients; patients with cancer such as Hodgkin's disease or lymphoma; and patients with autoimmune conditions being treated with mycophenolate mofetil or a biologic such as natalizumab, rituximab, or efalizumab. Such autoimmune conditions include, but are not limited to multiple sclerosis (MS), rheumatoid arthritis (RA), and systemic lupus erythematosis (SLE). Elderly patients with weakened immune systems that have or are suspected of having a latent polyomavirus infection are also at risk of developing a disease associated with a polyomavirus.

Polyomaviruses are non-enveloped, double-stranded DNA viruses. The DNA comprises an early coding region and a late coding region. The early region encodes two oncoproteins called large T antigen (T-Ag) and small t antigen (t-Ag). The late region encodes three capsid proteins, VP1, VP2, and VP3. In some polyomaviruses, the late region also encodes a small small regulatory protein called agnoprotein. Examples of human polyomaviruses that do not encode agnoprotein are: KI virus (KIV), WU virus (WUV), Merkel cell virus (MCV or MCPyV), B-cell lymphotropic polyomavirus (LPV); TSV; HPyV6; HPyV7; and HPyV9.

The methods of the invention comprise detection of a polyomavirus agnoprotein or agnoprotein antibodies and therefore may be practiced with any polyomavirus encoding an agnoprotein. Polyomaviruses currently known in the art can infect avians and mammals. The invention is preferably carried out with agnoprotein-encoding polyomaviruses that infect mammals, more preferably agnoprotein-encoding polyomaviruses that infect primates and more preferably still, agnoprotein-encoding polyomaviruses that infect humans. Exemplary agnoprotein-encoding polyomaviruses include, but are not limited to, JC virus (JCV); BK virus (BKV); simian virus 40 (SV40) (which is also found in humans); bovine polyomavirus (BPyV); simian virus 12 (SV12); squirrel monkey polyomavirus (SquiPyV); baboon polyomavirus 1 (formerly simian agent 12; SA12); and chimpanzee polyomavirus (ChPyV). JCV and BKV are exemplary human agnoprotein-encoding polyomaviruses and are preferred in the practice of the invention. In an embodiment, the method is practiced with JCV agnoprotein. In another embodiment, the method is practiced with a BKL agnoprotein. In yet another embodiment, the method is practiced with a combination of two or more agnoproteins, such JCV agnoprotein and BKL agnoprotein.

A number of diseases have been associated with polyomaviruses. In humans, progressive multifocal leukoencephalopathy (PML), neural tumors such as medulloblastoma, oligodendroglioma, astroglioma, and glioblastoma, and colorectal cancer have been associated with JC virus. PML has been detected in at-risk patients including: AIDS patients; patients on chronic immunosuppressive treatment regimens, such as organ transplant patients; patients with cancer such as Hodgkin's disease or lymphoma; and patients with autoimmune conditions being treated with mycophenolate mofetil or a biologic such as natalizumab, rituximab, or efalizumab. BK virus has been associated with nephritis and/or nephropathy in patients who have undergone renal transplantation. BK virus has also been associated with prostate cancer. These polyomavirus-associated diseases are a significant part of graft loss. BK virus has also been associated with cystitis such as hemorrhagic and nonhemorrhagic cystitis in patients who have undergone a bone marrow or stem cell transplant.

Polyomavirus Reactivation

The invention provides a method for detection of polyomavirus reactivation in a biological sample of a patient having or suspected of having a latent polyomavirus infection. The method comprises determining the presence or absence of a polyomavirus agnoprotein and/or agnoprotein antibodies in the biological sample. The presence of the polyomavirus agnoprotein and/or agnoprotein antibodies is indicative of reactivation of the polyomavirus in the patient. In an embodiment, the method further comprises measuring the level of the polyomavirus agnoprotein or agnoprotein antibodies in the biological sample. That level is then compared to the level of the polyomavirus agnoprotein or agnoprotein antibodies, respectively, in a control sample. An elevated level of the polyomavirus agnoprotein or agnoprotein antibodies in the biological sample relative respectively to the level of polyomavirus agnoprotein or agnoprotein antibodies in the control sample is indicative of reactivation of the polyomavirus in the patient. The control sample can be a sample obtained from a single control subject that does not have polyomavirus reactivation, or can be a sample representative of a population of such control subjects. A control sample can also be a reference database of levels for that agnoprotein or antibodies against that agnoprotein in a population of control subjects that do not have polyomavirus reactivation. The reference database can be generated by measuring the same agnoprotein or agnoprotein antibodies under the same conditions in a representative population.

In another embodiment of the method for detection of polyomavirus reactivation, the level of the polyomavirus agnoprotein or agnoprotein antibodies in the biological sample is compared to the level of polyomavirus agnoprotein or agnoprotein antibodies respectively in a positive control sample. The positive control sample can be a sample obtained from a single positive control subject that has polyomavirus reactivation, or can be a sample representative of a population of such positive control subjects. A positive control sample can also be a reference database of levels for the agnoprotein of interest or antibodies against the agnoprotein of interest in a population of positive control subjects that have polyomavirus reactivation.

Active Polyomavirus Infection

The invention also provides a method for diagnosing an active polyomavirus infection in a patient. The method comprises determining the presence or absence of a polyomavirus agnoprotein and/or agnoprotein antibodies in a biological sample from the patient. The presence of the polyomavirus agnoprotein and/or agnoprotein antibodies is indicative of an active polyomavirus infection in the patient.

In an embodiment, the method further comprises measuring the level of the polyomavirus agnoprotein or agnoprotein antibodies in the biological sample. That level is then compared to the level of the polyomavirus agnoprotein or agnoprotein antibodies, respectively, in a control sample. An elevated level of the polyomavirus agnoprotein or agnoprotein antibodies in the biological sample relative to the level of polyomavirus agnoprotein or agnoprotein antibodies respectively in the control sample is indicative of an active polyomavirus infection in the patient. The control sample can be a sample obtained from a single control subject that does not have an active polyomavirus infection or can be a sample representative of a population of such control subjects. A control sample can also be a reference database of levels for the agnoprotein of interest or antibodies against the agnoprotein of interest in a population of control subjects that do not have an active polyomavirus infection. The reference database can be generated by measuring the same agnoprotein or antibodies against the same agnoprotein under the same conditions in a representative population.

In another embodiment of the method for diagnosing an active polyomavirus infection in a patient, the level of the polyomavirus agnoprotein or agnoprotein antibodies in the biological sample is compared to the level of polyomavirus agnoprotein or agnoprotein antibodies respectively in a positive control sample. The positive control sample can be a sample obtained from a single positive control subject that has an active polyomavirus infection, or can be a sample representative of a population of such positive control subjects. A positive control sample can also be a reference database of levels for the agnoprotein or interest or antibodies against the agnoprotein of interest in a population of positive control subjects that have an active polyomavirus infection.

Establishing a threshold to distinguish between two possibilities, such as a normal level in a biological sample and an increased level in a biological sample, is well known to skilled artisan. Receiver operating characteristic (ROC) curve analysis is commonly used in this regard. See, for instance, Fawcett (2006) Pattern Recognition Letters 27:861-874); Pasanen et al. (1993, Br J Cancer. 67(4): 852-855.); and Greiner et al. (2000) Prev Vet Med. 30:23-41. Establishing a threshold is conventional in the development of diagnostic assays. For instance, as the skilled artisan is aware, the accuracy of a diagnostic test is commonly measured by its sensitivity and specificity. The skilled artisan is well aware that distributions of data from healthy and diseased persons almost always overlap (see, for instance, page 6 of Sacher et al., Widmann's Clinical Interpretation of Laboratory Tests, "Principles of Interpretation of Laboratory Tests", 11th edition, F. A. Davis Company, Philadelphia, Pa., 2000, pp. 3-27). As discussed in Sacher et al., the region of overlap concerns "false positives" in the healthy group and "false negatives" in the diseased group. Sensitivity and specificity, which are calculated based on a threshold value separating values identified as "healthy" and values identified as "diseased" (Ibid, pp. 5-6, FIG. 1-1 and text), describe the frequency of such false negatives and false positives, respectively, for a diagnostic dataset. While the ideal diagnostic test would have both specificity and sensitivity of 100%, that is, a test with no false positives and no false negatives, this high standard cannot generally be met (Ibid, p. 6, final paragraph). That is, the typical diagnostic test is for a likely diagnosis, not a definitive diagnosis. In some embodiments, the threshold level is a threshold value as discussed in Sacher et al. (ibid). In some embodiments herein, the threshold is a threshold value selected for a high specificity. In other embodiments, the threshold level is a threshold value selected for a high sensitivity.

It is contemplated that the amount of agnoprotein or agnoprotein antibodies in a biological fluid is proportional to the extent or degree of infection, for instance, the number of cells actively infected by polyomavirus and/or the rate of polyomavirus transcription and translation. Accordingly, a method of monitoring a polyomavirus infection over time in a patient diagnosed with an active polyomavirus infection is also provided. The method comprises assessing the level of a polyomavirus agnoprotein and/or agnoprotein antibodies in a first biological sample obtained from the patient at a first point in time to obtain a baseline level. The method further comprises assessing the level of polyomavirus agnoprotein or agnoprotein antibodies in a second biological sample obtained at a second point in time from the patient to obtain a second level. The second level is compared to the first level in order to identify whether the level of the biomarker is changing. If the second level is greater than the baseline level, the polyomavirus infection in the patient has progressed. Assays detecting agnoprotein antibodies optionally comprise determining the type of antibodies detected, such as IgG or IgM.

Risk of Polyomavirus-Associated Disease

As discussed elsewhere herein, polyomavirus reactivation can lead to the development of diseases such as PML. Accordingly, the invention also provides a method for assessing risk of developing a disease associated with a polyomavirus in an at-risk patient. The method comprises determining the presence or absence of a polyomavirus agnoprotein and/or agnoprotein antibodies in a biological sample from the at-risk patient. The presence of the polyomavirus agnoprotein and/or agnoprotein antibodies in the biological sample is indicative of increased risk of developing a disease associated with the polyomavirus.

The invention also provides a method of monitoring risk of developing a polyomavirus-associated disease in a patient as a function of time. The method comprises assessing the level of polyomavirus agnoprotein and/or agnoprotein antibodies in a first biological sample obtained from the at-risk patient at a first point in time to establish a baseline level of the agnoprotein biomarker. The method further comprises assessing the level of the agnoprotein or agnoprotein antibodies at a second point in time in a biological sample obtained from the at-risk patient at a second time in order to identify whether the level of the respective marker is changing. If the second level is greater than the baseline level, the patient has an increased risk of developing a disease associated with the polyomavirus. The second assessing step is generally performed at least one day after the baseline assessment. It can also be performed multiple days, weeks, months or years after the baseline assessment. Moreover, the second assessing step can be performed iteratively over time to acquire additional data and thereby monitor the risk. In an embodiment, the disease is PML and the agnoprotein is a JCV agnoprotein.

In some embodiments of the methods for assessing or monitoring risk of developing a polyomavirus-associated disease, the at-risk patient is selected from as AIDS patient, a patient undergoing immunosuppression therapy, and an immunocompromised patient. In some embodiments, the polyomavirus is JC virus and the polyomavirus-associated disease is at least one of PML, and a tumor such as oligodendroglioma, astroglioma, glioblastoma, and colon cancer. In some embodiments, the polyomavirus is BK virus and the polyomavirus-associated disease prostate cancer. In some embodiments, the at-risk patient is selected from a renal transplant patient or a bone marrow or stem cell transplant patient. In these embodiments, the polyomavirus is BK virus and the polyomavirus-associated disease is nephritis and/or nephropathy.

Assay methods used in the practice of the invention may utilize a substance comprising a binding agent that is specific for agnoprotein. Binding agents can be prepared, using conventional methods in the art, to bind specifically to any polyomavirus agnoprotein. There are a vast number of protein sequences for polyomavirus agnoproteins known in the art. For instance, exemplary agnoprotein protein sequences are readily available in public sequence databases, such as National Library of Medicine's genetic sequence database GENBANK® (Benson et al., 2008, Nucleic Acids Research, 36(Database issue):D25-30). Exemplary polyomavirus agnoprotein sequences include, but are not limited to the following: JC virus (JCV)—GENBANK® accession nos. AAB62686.1, AAB62681.1, AAA82098.1, AAF04092.1, AAK70231.1, AAF04090.1, AAG30854.1, and AAG37195.1; BK virus (BKV)—GENBANK® accession nos. AAA46879.1, AAT47410.1, AAT47404.1, AE089560.1, and YP_717936.1; simian virus 40 (SV40)—GENBANK® accession no. YP_003708378.1; bovine polyomavirus (BPyV)—GENBANK® accession no. NP_040784.1; simian virus 12 (SV12)—GENBANK® accession no. YP_002635563.1; squirrel monkey polyomavirus (SquiPyV)—GENBANK® accession no. CA003079.1; Baboon polyomavirus 1 (SA12)—GENBANK® accession no. YP_406551.1; and chimpanzee polyomavirus (ChPyV)—GENBANK® accession no. CBX23441.1, each of which is incorporated by reference herein.

It is well-known in the art that proteins can exist in a biological sample in a plurality of different forms. These forms can result from either or both of pre- and post-translational modifications. Pre-translationally modified forms include allelic variants, splice variants and RNA editing forms. Post-translationally modified forms include forms resulting from proteolytic cleavage (e.g., cleavage of a signal sequence or fragments of a parent protein), glycosylation, phosphorylation, lipidation, oxidation, methylation, cysteinylation, sulphonation and acetylation.

Thus, in addition to the exemplary agnoprotein sequence identified herein by name or accession number, the invention also contemplates the detection in a body fluid sample of naturally-occurring variants that are at least 90%, at least 95%, at least 96%, at least 97%, at least 98%, or at least 99% identical to the exemplified biomarker sequences. Detection of such naturally-occurring variants in a biological fluid sample of a subject may be used in the methods described and claimed.

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site having the universal resource locator. "blast(dot)ncbi(dot)nlm(dot)nih(dot)gov/Blast(dot)cgi". BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAT) can be used.

In some embodiments of the methods of the invention, a biological sample can be assayed for the presence of a polyomavirus agnoprotein. Assay methods may utilize a substance comprising a binding agent that is specific for agnoprotein. In one embodiment, the substance comprises a collection of binding agents specific for two or more different agnoproteins. The different agnoproteins may be different variants of the same type of polyomavirus such as variants of JCV agnoprotein, and/or may be agnoproteins from different types of polyomavirus such as JCV and BKV.

In some embodiments, the methods of the invention can be carried out by detection of agnoprotein antibodies in a biological sample. Detection of agnoprotein antibodies in the biological sample can be performed using conventional methods in the art. Examples of such methods include, but is not limited to, ELISA, agglutination, precipitation, complement-fixation, and fluorescent antibodies. In some embodiments, detection of agnoprotein antibodies comprises combining the biological fluid with a composition comprising polyomavirus agnoprotein and/or an antigenic fragment thereof under suitable conditions to antibodies in the biological fluid to bind to the agnoprotein and/or antigenic fragments thereof to form an antibody-antigen complex, and then detecting the antibody-antigen complex. In some embodiments, agnoprotein antibodies can be detected using an agglutination assay.

Assays based on protein-specific biomolecule interaction include, but are not limited to, antibody-based assays, aptamer-based assays, receptor and ligand assays, enzyme activity assays, and allosteric regulator binding assays. The invention is not limited to any one method of protein detection, but rather encompasses all presently known or heretofore unknown methods, such as methods that are discovered in the art. Proteins may be detected by other methods, e.g., mass spectroscopy analysis, that do not relying on a binding moiety.

In one embodiment, the binding moiety comprises an antibody that specifically binds to agnoprotein. Antibodies can be used in various immunoassay-based protein determination methods such as Western blot analysis, immunoprecipitation, radioimmunoassay (RIA), immunofluorescent assay, chemiluminescent assay, flow cytometry, immunocytochemistry and enzyme-linked immunosorbent assay (ELISA).

In an enzyme-linked immunosorbent assay (ELISA), an enzyme such as, but not limited to, horseradish peroxidase (HRP), alkaline phosphatase (AP), beta-galactosidase or urease can be linked, for example, to an antigen antibody or to a secondary antibody for use in a method of the invention. A horseradish-peroxidase detection system may be used, for example, with the chromogenic substrate tetramethylbenzidine (TMB), which yields a soluble product in the presence of hydrogen peroxide that is detectable at 450 nm. Other convenient enzyme-linked systems include, for example, the alkaline phosphatase detection system, which may be used with the chromogenic substrate p-nitrophenyl phosphate to yield a soluble product readily detectable at 405 nm. Similarly, a beta-galactosidase detection system may be used with the chromogenic substrate o-nitrophenyl-beta-D-galactopyranoside (ONPG) to yield a soluble product detectable at 410 nm. Alternatively, a urease detection system may be used with a substrate such as urea-bromocresol purple (Sigma Immunochemicals, St. Louis, Mo.). Useful enzyme-linked primary and secondary antibodies can be obtained from any number of commercial sources.

For chemiluminescence and fluorescence assays, chemiluminescent and fluorescent secondary antibodies may be obtained from any number of commercial sources. Fluorescent detection is also useful for detecting antigen or for determining a level of antigen in a method of the invention. Useful fluorochromes include, but are not limited to, DAPI, fluorescein, Hoechst 33258, R-phycocyanin, B-phycoerythrin, R-phycoerythrin, rhodamine, Texas red and lissamine-Fluorescein- or rhodamine-labeled antigen-specific antibodies.

Radioimmunoassays (RIAs) are described for example in Brophy et al., 1990, *Biochem. Biophys. Res. Comm.* 167: 898-903 and Guechot et al., 1996, *Clin. Chem.* 42:558-563. Radioimmunoassays are performed, for example, using Iodine-125-labeled primary or secondary antibody.

Western blotting may also be used to detect and or determine the level of phosphorylated Cdc27. Western blots may be quantified using well known methods such as scanning densitometry (Parra et al., 1998, *J. Vasc. Surg.* 28:669-675).

A signal emitted from a detectable antibody is analyzed, for example, using a spectrophotometer to detect color from a chromogenic substrate; a radiation counter to detect radiation, such as a gamma counter for detection of Iodine-125; or a fluorometer to detect fluorescence in the presence of light of a certain wavelength. Where an enzyme-linked assay is used, quantitative analysis of the amount of antigen is performed using a spectrophotometer. It is understood that the assays of the invention can be performed manually or, if desired, can be automated and that the signal emitted from multiple samples can be detected simultaneously in many systems available commercially. Antigen-antibody binding can also be detected, for example, by mass spectrometry.

The antibody used to detect agnoprotein in a sample in an immunnoassay can comprise a polyclonal or monoclonal antibody. The antibody can comprise an intact antibody, or antibody fragments capable of specifically binding antigen. Such fragments include, but are not limited to, Fab and F(ab')$_2$ fragments.

Techniques for detecting and quantifying (such as with respect to a control) antibody binding are well-known in the art. Antibody binding to agnoprotein may be detected through the use of chemical reagents that generate a detectable signal that corresponds to the level of antibody binding and, accordingly, to the level of marker protein expression. Examples of such detectable substances include enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{35}$S, or $^{3}$H.

Antibody binding may be detected through the use of a secondary antibody that is conjugated to a detectable label. Examples of detectable labels include but are not limited to polymer-enzyme conjugates. The enzymes in these complexes are typically used to catalyze the deposition of a chromogen at the antigen-antibody binding site, thereby resulting in cell staining that corresponds to expression level of the biomarker of interest. Preferred enzymes of particular interest include horseradish peroxidase (HRP) and alkaline phosphatase (AP).

Agnoprotein can be detected and quantified by aptamer-based assays, which are very similar to antibody-based assays, but with the use of an aptamer instead of an antibody. An "aptamer-based" assay is thus an assay for the determination of polypeptide that relies on specific binding of an aptamer. An aptamer can be any polynucleotide, generally a RNA or a DNA, which has a useful biological activity in terms of biochemical activity or molecular recognition attributes. Usually, an aptamer has a molecular activity such as having an enzymatic activity or binding to a polypeptide at a specific region (i.e., similar to an epitope for an antibody) of the polypeptide. It is generally known in the art that an aptamer can be made by in vitro selection methods. In vitro selection methods include a well known method called systematic evolution of ligands by exponential enrichment (a.k.a. SELEX). Briefly, in vitro selection involves screening a pool of random polynucleotides for a particular polynucleotide that binds to a biomolecule, such as a polypeptide, or has a particular activity that is selectable. Generally, the particular polynucleotide represents a very small fraction of the pool, therefore, a round of amplification, usually via polymerase chain reaction, is employed to increase the representation of potentially useful aptamers. Successive rounds of selection and amplification are employed to exponentially increase the abundance of a particular aptamer. In vitro selection is described in Famulok and Szostak, *Angew. Chem.*, 1992, 104, 1001. (*Angew. Chem. Int. Ed. Engl.* 1992, 31, 979-988.); Famulok and Szostak, *Nucleic Acids and Molecular Biology*, Vol 7, F. Eckstein, D. M. J. Lilley, Eds., Springer Verlag, Berlin, 1993, pp. 271; Klug and Famulok, *Mol. Biol. Reports* 1994, 20, 97-107; and Burgstaller and Famulok, *Angew. Chem.* 1995, 107, 1303-1306 (*Angew. Chem. Int. Ed. Engl.* 1995, 34, 1189-1192); U.S. Pat. Nos. 6,287,765, 6,180,348, 6,001,570, 5,861,588, 5,567,588, 5,475,096, and 5,270,163.

Substantially pure agnoprotein, which can be used as an immunogen for raising polyclonal or monoclonal antibodies, or as a substrate for selecting aptamers, or for binding agnoprotein antibodies present in a biological sample, can be prepared, for example, by recombinant DNA methods. For example, the cDNA of the marker protein can be cloned into an expression vector by techniques within the skill in the art. An expression vector comprising sequences encoding the marker protein can then be transfected into an appropriate eukaryotic host, whereupon the protein is expressed. The expressed protein can then be isolated by any suitable technique. In some embodiments, antigenic fragments of agnoprotein can be used. Antigenic fragments of a polyomavirus agnoprotein can be readily identified by the skilled artisan using methods known in the art. Polyomavirus agnoprotein is a type II integral membrane protein, thus the N-terminal portion of the protein comprise the intracellular domain. Examples of agnoprotein fragments contemplated to be antigenic fragments include a fragment comprising or consisting essentially of the extracellular domain, a fragment comprising or consisting essentially of the transmembrane domain and a fragment comprising or consisting essentially of the intracellular domain. The domains can be predicted by programs known in the art for predicting transmembrane domains.

Agnoprotein can be detected by any of the well-known mass spectrometry methods.

In some embodiments of the methods of the invention, the method further comprises assaying a first control composition that does not contain agnoprotein, or agnoprotein antibodies, and a second control composition that does contain agnoprotein, or angoprotein antibodies. Such assays and other steps performed to verify, for instance, the integrity of the substance used to detect agnoprotein, or agnoprotein antibodies, as well as the integrity of the of biological sample, are conventional in the art.

The methods for detecting agnoprotein or agnoprotein antibodies can be readily adapted to kit form. A kit may contain a set of reagents that specifically detects for detection of agnoprotein, or agnoprotein antibodies and one or more reagents and/or diluents for facilitating the contact of the reagent and agnoprotein or agnoprotein antibodies in the sample. The kit may further comprise instructions for using the kit according to the present invention. The reagent may comprise, for example, an antibody or aptamer specific for agnoprotein, or may comprise agnoprotein or a antigenic fragments thereof. The agnoprotein, antibody or aptamer may be detectably labeled, as described above. The kit can further comprise components necessary for detecting the detectable label (e.g., an enzyme or a substrate), and instrumentation for detection and measurement.

The kit can comprise, for example: (1) a first antibody (e.g., attached to a solid support) that binds to a marker protein; and, optionally, (2) a second, different antibody that binds to either the protein or the first antibody and is conjugated to a detectable label.

The kit may further comprise one or more buffers and/or reagents, e.g., labeling buffer and/or reagents, and detection means for detecting a detectable label. Protocols for using these buffers and reagents for performing different steps of the procedure may also be included in the kit.

Reagents may be supplied in a solid (e.g., lyophilized) or liquid form. Kits of the present invention may optionally comprise different containers (e.g., vial, ampoule, test tube, flask or bottle) for each individual buffer and/or reagent. Each component will generally be suitable as aliquoted in its respective container or provided in a concentrated form. Other containers suitable for conducting certain steps for the disclosed methods may also be provided. In certain embodiments, the kits of the present invention further comprise control samples.

The instructional material may comprise a publication, a recording, a diagram, or any other medium of expression which can be used to communicate the usefulness of the method. The package insert may comprise text housed in any physical medium, e.g., paper, cardboard, film, or may be housed in an electronic medium such as a diskette, chip, memory stick or other electronic storage form. The instructional material of the kit of the invention may, for example, be affixed to a container which contains other contents of the kit, or be shipped together with a container which contains the kit. Alternatively, the instructional material may be shipped separately from the container with the intention that the instructional material and the contents of the kit be used cooperatively by the recipient.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

Example 1: Agnoprotein Detection in Growth Media from JCV-Infected Cells

Figure 1:
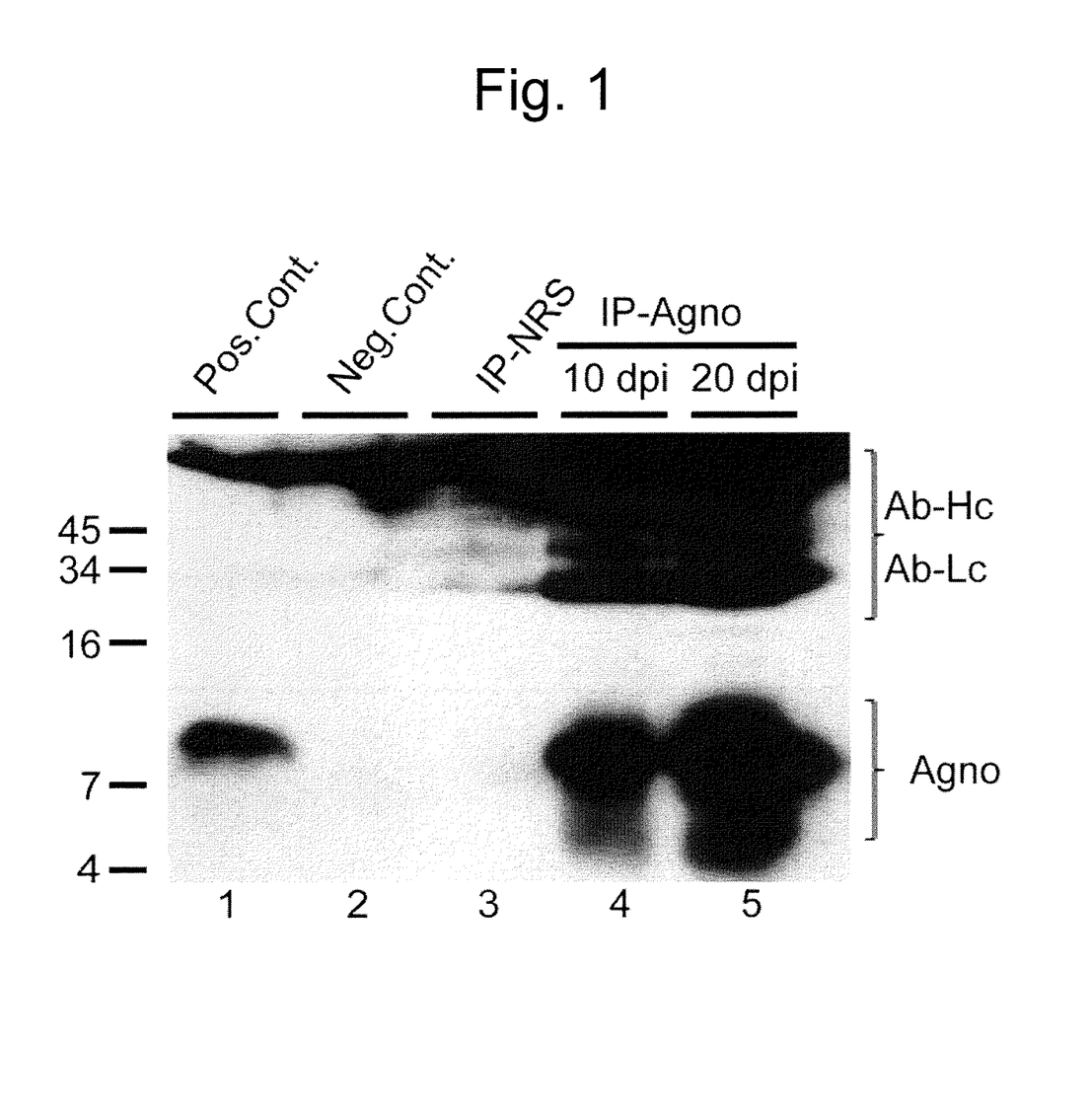
FIG. 1 is a western blot of the detection of agnoprotein in the growth medium of SVG-A cells infected with the Mad-1 strain of JC virus. Agnoprotein is expressed by infected cells (lane 1) and present in growth media (lane 4, 10 days post infection: lane 5, 20 days post infection) Also shown in FIG. 1 are results for normal rabbit serum (lane 3, IP-NRS), and positive (lane 1) and negative (lane 2) controls. Heavy (AB-Hc) and light (AB-Lc) chains of antibody used in the assay are marked.

To determine the secretion of JCV agnoprotein from infected cells, SVG-A cells were first infected with the Mad-1 strain of JC virus, which was isolated from a patient with the demyelinating disease, progressive multifocal leukoencehalopathy (PML). The initial cycle of JCV infection takes up to 20 days, and agnoprotein expression can be detected as early as 10 day post infection. SVG-A cells are a subclone of the original SVG human glial cell line established by transformation of human fetal glial cells by an origin-defective SV40 mutant (Major et al., *Proc. Natl. Acad. Sci. USA* 82:1257-1261, 1985. Growth media from cells was collected at 10 and 20 days post infection (dpi). The collected growth media was centrifuged at 5K for 15 min. to clear cellular debris. The supernatant was collected and denatured at 95° C. In parallel, whole cell extracts were used as positive controls. To determine the presence of agnoprotein in the growth media, an immunoprecipitation assay was performed using an antibody specific for agnoprotein. As shown in FIG. 1, agnoprotein is expressed by infected cells (lane 1) and present in growth media (lane 4, 10 days post infection: lane 5, 20 days post infection) indicating that agnoprotein is secreted from infected cells. Also shown in FIG. 1 are results of the immunoprecipitation assay for normal rabbit serum (Lane 3, IP-NRS) and positive (lane 1) and negative (lane 2) controls.

Example 2: Secretion of Agnoprotein by Agnoprotein-Expressing Cells

The following study demonstrates that agnoprotein can be detected in soluble form in the growth media of cells which actively replicate a polyomavirus, JCV, and that the appearance of agnoprotein in the growth medium is not simply due to the mechanical destruction of the cell membrane by the viral particles at the stage of release from the cells.

Figure 2:
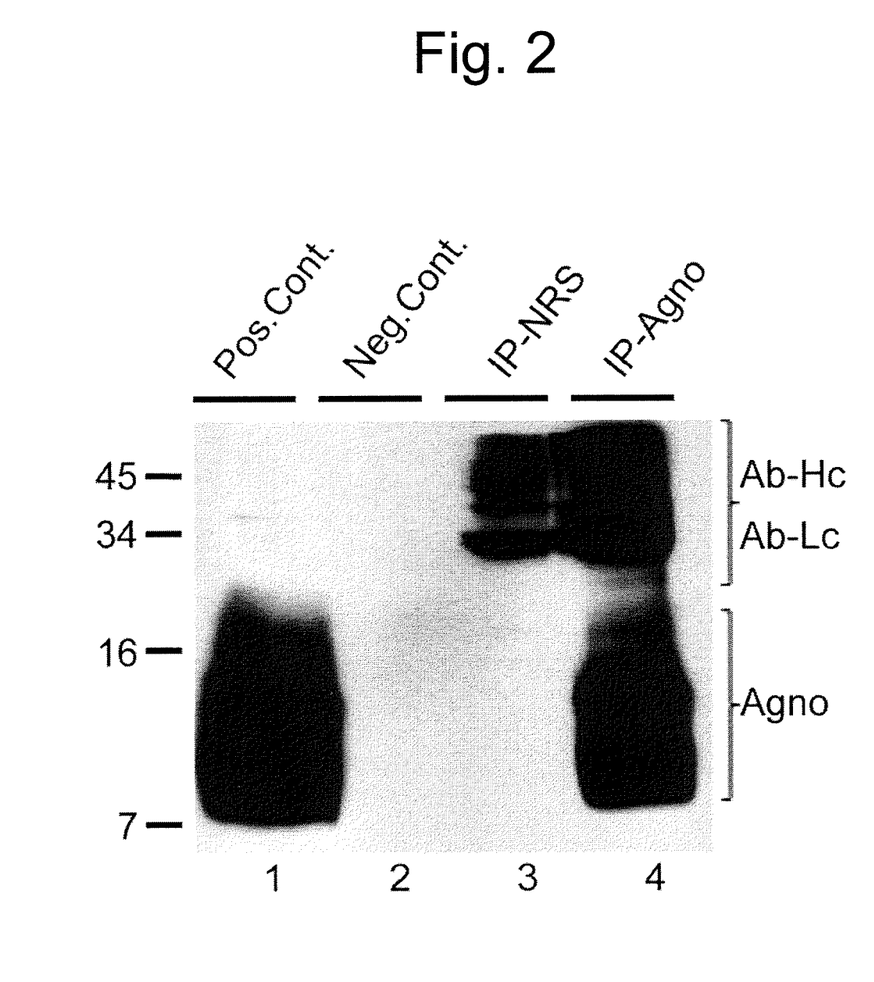
FIG. 2 is a western blot of growth medium from the culture of human oligodendroglioma Tc620 cells infected with replication defective adenovirus encoding JCV agnoprotein. Agnoprotein was immunoprecipitated from growth media with an agnoprotein specific antibody (IP-Agno, lane 4), but not with normal rabbit serum (IP-NRS, lane 3). Whole cell extracts from cells infected with virus expressing agnoprotein (lane 1) and cells infected with adenovirus not encoding agnoprotein (lane 2) were used as positive and negative controls, respectively. Heavy (AB-Hc) and light (AB-Lc) chains of antibody used in the assay are marked.

Human oligodendroglioma Tc620 cells were infected with replication defective adenovirus encoding JCV agnoprotein. Control cells were infected with adenovirus not encoding agnoprotein. Growth media was collected at 48 hour post-transfections simultaneously along with whole cell extracts. Five ml culture media was used in immunoprecipitations. Whole cell extracts were loaded as positive (lane 1) and negative (lane 2) controls of the detection (FIG. 2). Agnoprotein was transiently expressed in Tc620 cells in the absence of any lytic viral infection. Growth medium was collected and centrifuged at 5K for 15 min., and the supernatant collected for immunoprecipitation assay. As shown in FIG. 2, agnoprotein was immunoprecipitated from growth media with an agnoprotein specific antibody (IP-Agno, lane 4), but not with normal rabbit serum (IP-NRS, lane 3). Thus, agnoprotein is secreted from agnoprotein-expressing cells into the extracellular space.

Example 3: ELISA Based Detection Assay for Agnoprotein

Figure 3A:
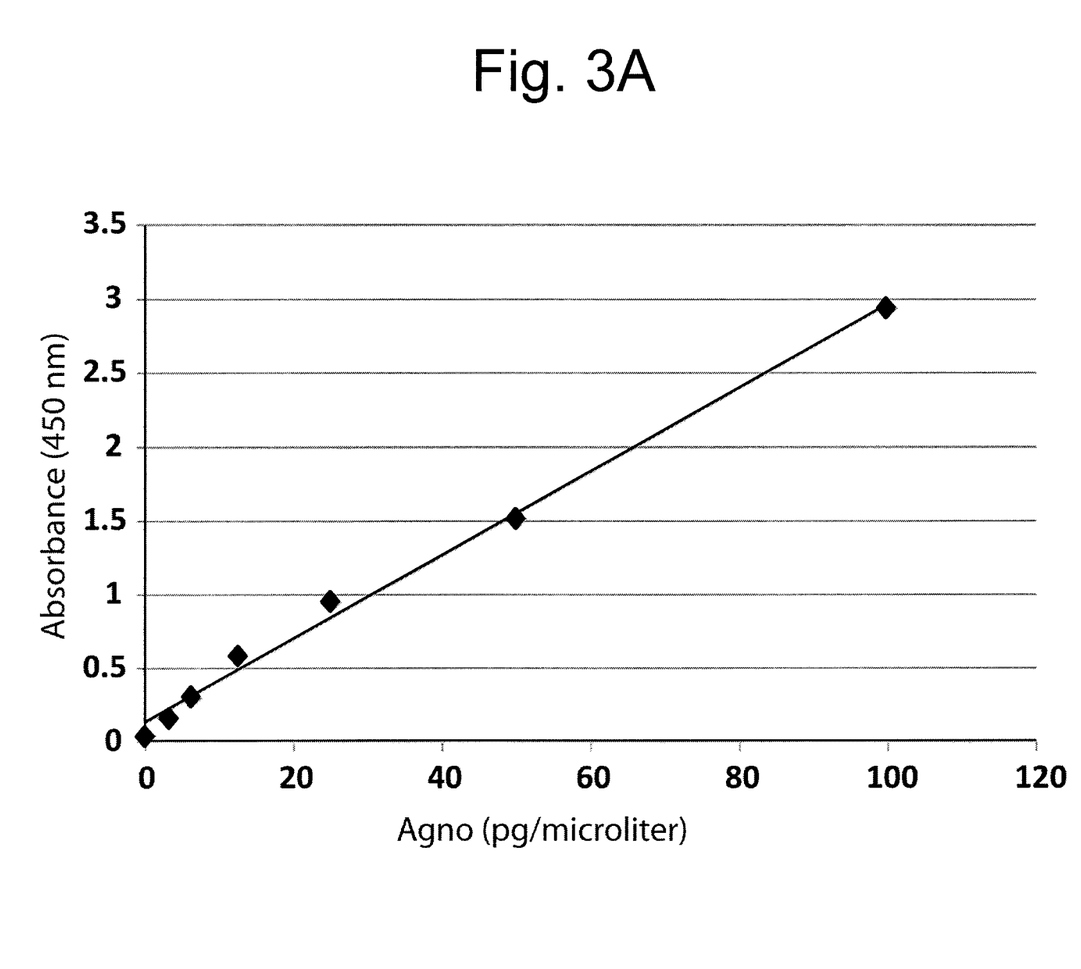
FIG. 3A is a plot of an enzyme-linked immunosorbent assay (ELISA) of agnoprotein in the cell growth medium supplemented with increasing concentrations of recombinant agnoprotein fused to MBP.
Figure 3B:
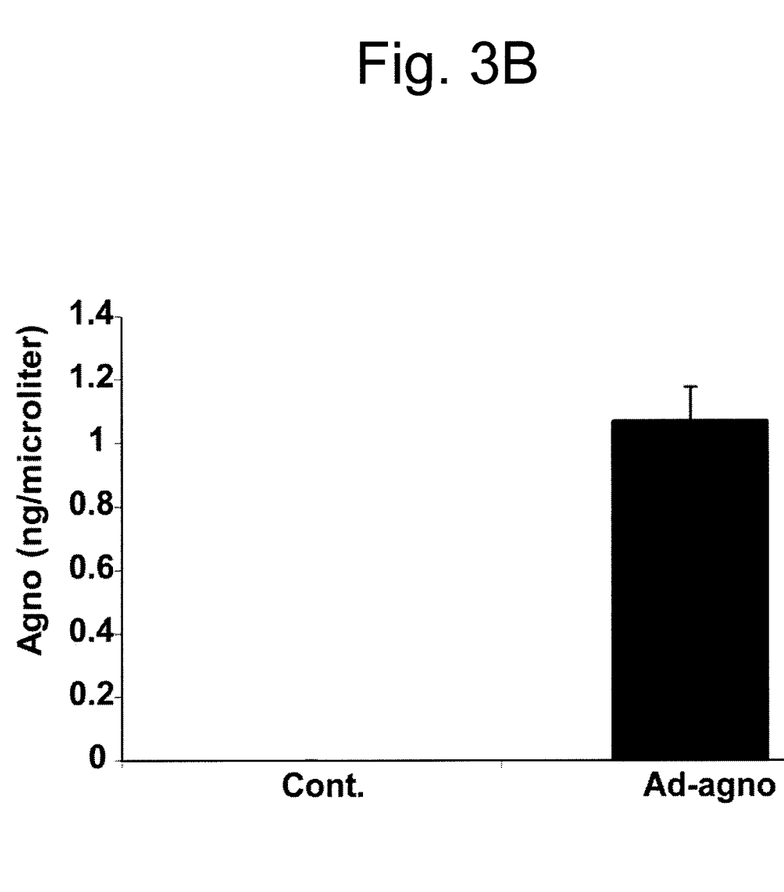
FIG. 3B is a graph showing conditioned media from cells expressing agnoprotein testing positive for the agnoprotein (Ad-agno) whereas conditioned-media from control cells (Cont.) showed no reactivity.

To establish a detection system for agnoprotein, agnoprotein was expressed and purified in *E. coli* as fused to MBP (MBP-agno). The purified-MBP-agno was utilized for standardization of an enzyme-linked immunosorbent assay (ELISA) for the detection of agnoprotein by using an agnoprotein-specific antibody (FIG. 3A). In order to quantify the amount of the agnoprotein, conditioned-media from agnoprotein-expressing cells was first tested. Conditioned media was obtained from either adeno-null (cont.) or adeno-agno (Ad-agno) infected Tc620 cells. As shown in FIG. 3B, conditioned media from cells expressing agnoprotein was assayed positive for the agnoprotein (~1 ng/µl) whereas the conditioned-media from control cells showed no reactivity, indicating that the ELISA-based assay can specifically detect and quantify agnoprotein.

Example 4: Agnoprotein Detection PML and MS Patient Samples

Figure 4A:
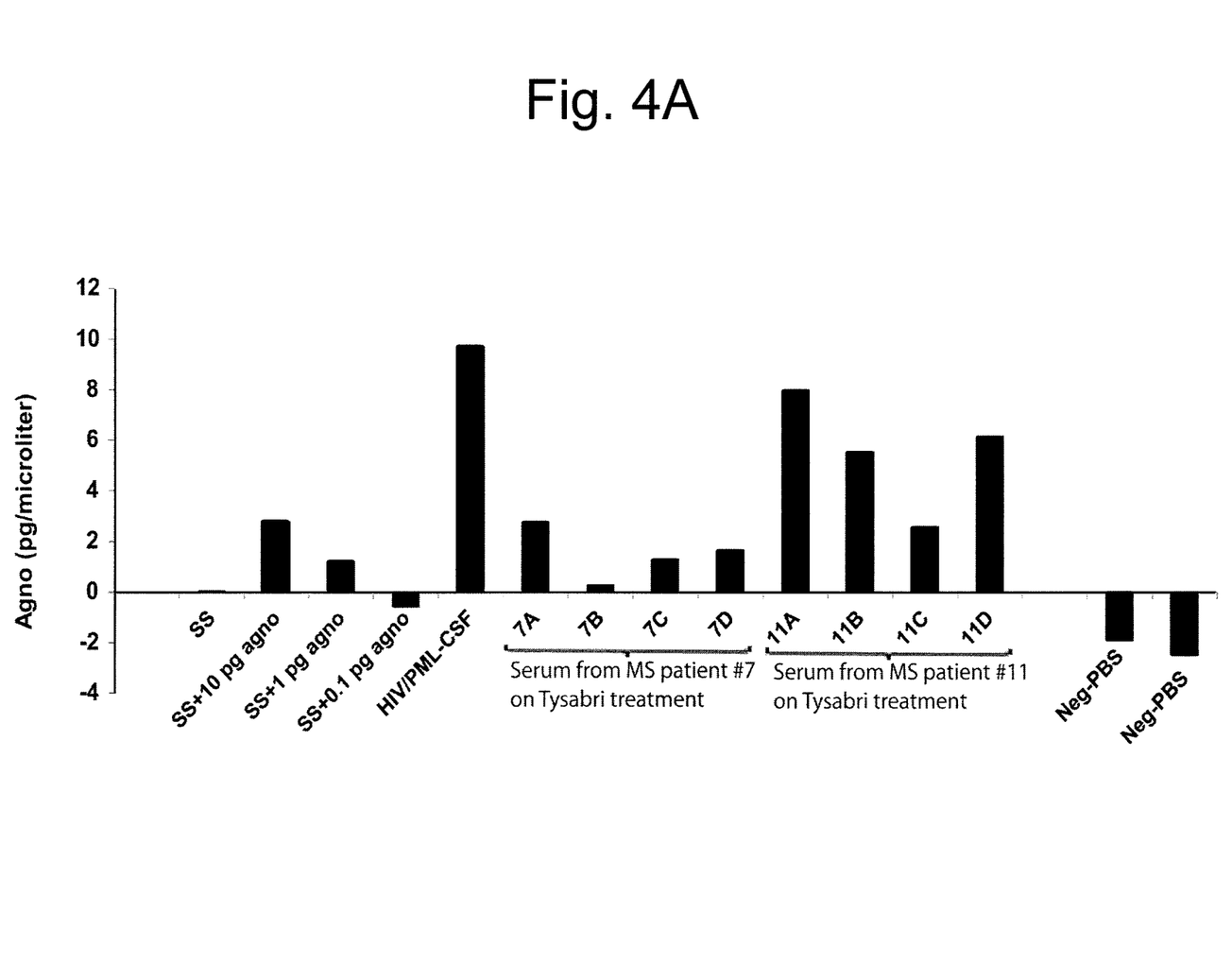

A cerebrospinal fluid (CSF) sample was obtained from a PML case developed in an HIV-AIDS patient and subject to agnoprotein ELISA. Serum samples were also obtained from serum samples from two MS patients at different stages of disease taking natalizumab (TYSABRI®) monoclonal antibody therapy for MS. Natalizumab treatment in MS patients is a risk factor for the reactivation of JC virus and the development of PML (Kappos et al., *The Lancet Neurology*, 6(5):431-441, 2007). As shown in FIG. 4A, agnoprotein was detected in the CSF sample (HIV/PML-CSF) indicating that agnoprotein serves as a marker of PML development. The serum samples of MS patients were also positive for agnoprotein at all draw times of the treatment representing different stages of disease ((7A-D, and 11A-D). The quantity of the agnoprotein detected varied at different stage of the treatment. Recombinant agnoprotein at 10, 1 and 0.1 picogram concentrations was used as positive control (SS=10 pg agno; SS=1 pg agno; SS=0.10 pg agno). Serum sample from an healthy individual (SS) and PBS (Neg-PBS× 2) were used as negative controls of the experiment.

Figure 4B:
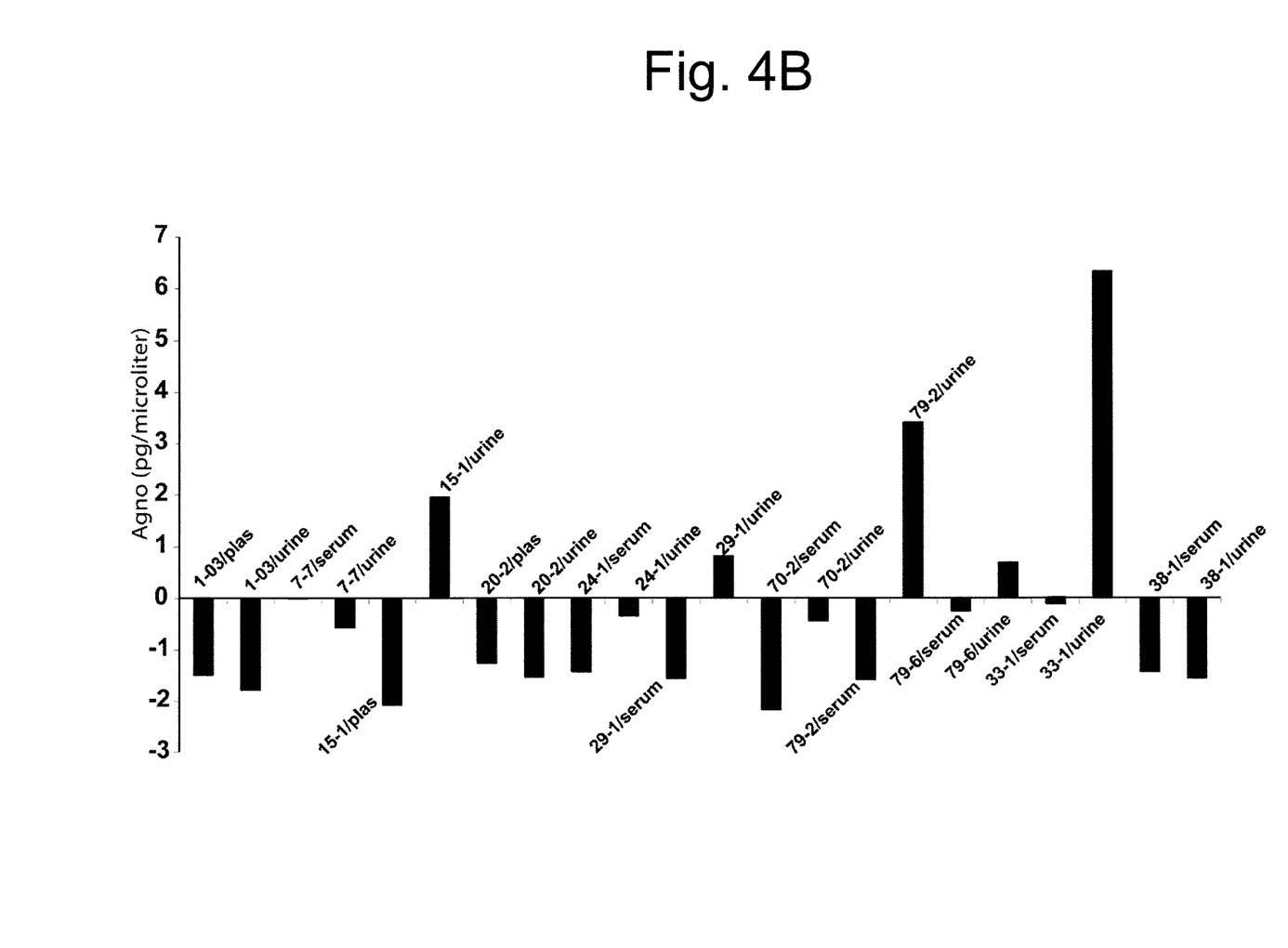
FIG. 4B shows the results of an agnoprotein enzyme-linked immunosorbent assay of human plasma, serum, and urine samples obtained from patients diagnosed with BKV-nephropathy.

Example 5: Presence of Aagnoprotein in Biological Samples Obtained from BKV-Nephropathy Patients Agnoprotein ELISA was performed on plasma, serum, and urine samples obtained from patients diagnosed with BKV-nephropathy, according to the procedure of Example 4. Five urine samples from 11 patients were positive for agnoprotein (FIG. 4B).

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method for detecting polyomavirus agnoprotein in a patient, said method comprising:
    obtaining a sample of a body fluid from a human patient; and
    detecting whether polyomavirus apoprotein is present in the sample by contacting the sample with a binding agent that specifically binds polyomavirus agnoprotein, and detecting binding between the agnoprotein and the binding agent.

2. The method according to claim 1 wherein the binding agent is an antibody or an aptamer.

3. The method according to claim 1 wherein the body fluid is blood.

4. The method according to claim 1 wherein the body fluid is blood serum.

5. The method according to claim 1 wherein the body fluid is blood plasma.

6. The method according to claim 1 wherein the body fluid is urine.

7. The method according to claim 1 wherein the body fluid is cerebrospinal fluid.

8. The method according to claim 1, wherein the agnoprotein is released by an infected cell of the human patient.

9. The method according to claim 1, wherein the agnoprotein is detected as early as ten days post infection with polyomavirus.

* * * * *